(12) United States Patent
Peter et al.

(10) Patent No.: US 7,066,909 B1
(45) Date of Patent: Jun. 27, 2006

(54) PROPELLING DEVICE FOR A PISTON IN A CONTAINER CONTAINING A LIQUID MEDICAMENT

(75) Inventors: Daniel Peter, Niederwangen (CH); Beat Kindler, Hasle-Ruegsau (CH)

(73) Assignee: Disetronic Licensing AG, Burgdorf (CH)

( * ) Notice: Subject to any disclaimer, the term of this patent is extended or adjusted under 35 U.S.C. 154(b) by 0 days.

(21) Appl. No.: 09/403,443

(22) PCT Filed: Apr. 22, 1998

(86) PCT No.: PCT/CH98/00157

§ 371 (c)(1),
(2), (4) Date: Dec. 13, 2000

(87) PCT Pub. No.: WO98/47552

PCT Pub. Date: Oct. 29, 1998

(30) Foreign Application Priority Data

Apr. 23, 1997 (DE) .............................. 197 17 107

(51) Int. Cl.
*A61M 5/20* (2006.01)
*A61M 5/00* (2006.01)

(52) U.S. Cl. .................. 604/136; 604/135; 604/211; 604/134

(58) Field of Classification Search ............. 604/211, 604/207, 232, 130–138, 198, 187, 186; 222/287, 222/391
See application file for complete search history.

(56) References Cited

U.S. PATENT DOCUMENTS

| 4,592,745 A | 6/1986 | Rex et al. |
|---|---|---|
| 4,865,591 A | 9/1989 | Sams |
| 4,883,472 A | 11/1989 | Michel |
| 4,946,446 A | 8/1990 | Vadher |
| 4,950,246 A | 8/1990 | Muller |
| 4,973,318 A | 11/1990 | Holm et al. |
| 5,017,190 A | 5/1991 | Simon et al. |
| 5,084,060 A | 1/1992 | Freund et al. |
| 5,114,406 A | 5/1992 | Gabriel et al. |
| 5,273,544 A * | 12/1993 | van der Wal ............... 604/134 |
| 5,279,579 A | 1/1994 | D'Amico |
| 5,279,585 A | 1/1994 | Balkwill |
| 5,292,314 A | 3/1994 | D'Alessio et al. |
| 5,295,976 A | 3/1994 | Harris |
| 5,320,609 A | 6/1994 | Haber et al. |
| 5,336,183 A | 8/1994 | Greelis et al. |
| 5,338,311 A | 8/1994 | Mahukar |
| 5,370,629 A | 12/1994 | Michel et al. |
| 5,472,430 A | 12/1995 | Vaillancourt et al. |
| 5,496,293 A | 3/1996 | Huggenberger |
| 5,514,097 A * | 5/1996 | Knauer ...................... 604/136 |
| 5,527,294 A | 6/1996 | Weatherford et al. |

(Continued)

FOREIGN PATENT DOCUMENTS

DE 3645245 11/1986

(Continued)

*Primary Examiner*—Nicholas D. Lucchesi
*Assistant Examiner*—Roz Maiorino
(74) *Attorney, Agent, or Firm*—Dorsey & Whitney LLP

(57) ABSTRACT

An apparatus for administering a substance, including a housing, a piston, a container and a propelling device, the propelling device including a base element, a first shifting stage shiftable relative to the base element, and a second shifting stage shiftable relative to the base element and to the first shifting stage and slaving the first shifting stage, wherein the propelling device, container and piston are operably coupled to the housing and the first shifting stage is in contact with the piston.

26 Claims, 13 Drawing Sheets

U.S. PATENT DOCUMENTS

| | | | |
|---|---|---|---|
| 5,549,558 A | 8/1996 | Martin | |
| 5,549,575 A | 8/1996 | Giambattista et al. | |
| 5,573,510 A | 11/1996 | Issacson | |
| 5,582,598 A | 12/1996 | Chanoch | |
| 5,591,136 A | 1/1997 | Gabriel | |
| 5,591,138 A | 1/1997 | Vaillancourt | |
| 5,593,390 A | 1/1997 | Castellano et al. | |
| 5,609,577 A | 3/1997 | Haber et al. | |
| 5,643,214 A | 7/1997 | Marshall et al. | |
| 5,658,259 A | 8/1997 | Pearson et al. | |
| 5,674,204 A * | 10/1997 | Chanoch | 604/207 |
| 5,679,111 A | 10/1997 | Hjertman et al. | |
| 5,725,508 A | 3/1998 | Chanoch et al. | |
| 5,728,074 A | 3/1998 | Castellano et al. | |
| 5,743,889 A | 4/1998 | Sams | |
| 5,807,346 A | 9/1998 | Frezza | |

FOREIGN PATENT DOCUMENTS

| | | |
|---|---|---|
| DE | C3638984 | 11/1986 |
| DE | 3900926 | 8/1989 |
| DE | 4223958 | 7/1992 |
| EP | 0037696 | 3/1981 |
| EP | 0058536 | 8/1982 |
| EP | 0245312 | 10/1986 |
| EP | 0268191 | 11/1987 |
| EP | 0298067 | 6/1988 |
| EP | B 327910 | 1/1989 |
| EP | 0373321 | 6/1990 |
| EP | A 496141 | 1/1991 |
| EP | 0516473 | 5/1992 |
| EP | 0498737 | 8/1992 |
| EP | 0554995 | 8/1993 |
| EP | 0594349 | 4/1994 |
| EP | 0627229 | 5/1994 |
| FR | 2701211 | 8/1994 |
| WO | WO 8702895 | 5/1987 |
| WO | WO 9110460 | 7/1991 |
| WO | WO 9305835 | 8/1992 |
| WO | WO 9218179 | 10/1992 |
| WO | WO 9316740 | 9/1993 |
| WO | WO 9409841 | 5/1994 |
| WO | WO 94/15560 | 7/1994 |
| WO | WO 9415210 | 7/1994 |
| WO | WO 9501812 | 1/1995 |
| WO | WO 9504563 | 2/1995 |
| WO | WO 9607443 | 3/1996 |
| WO | WO 97/00091 | 1/1997 |

* cited by examiner

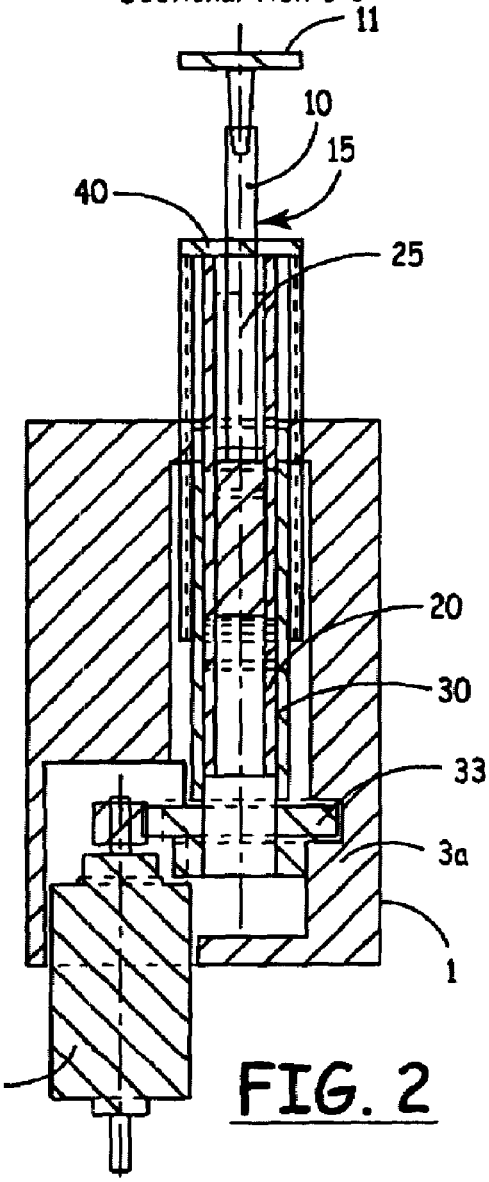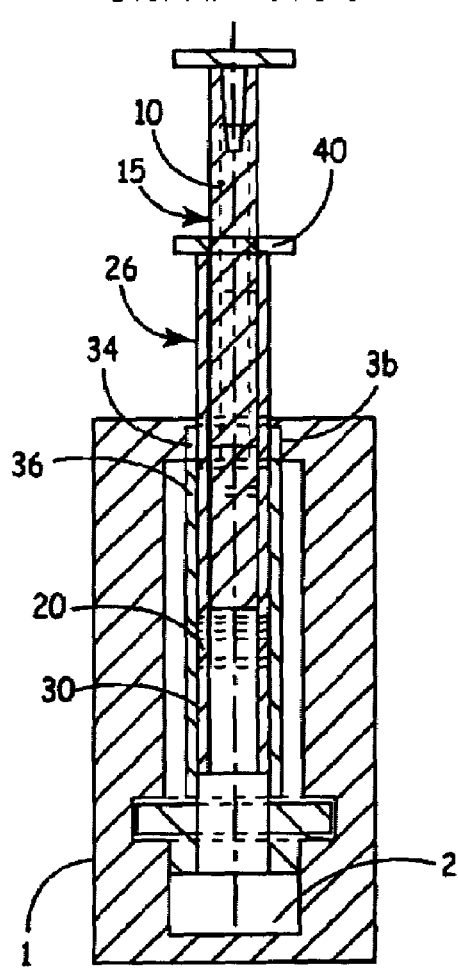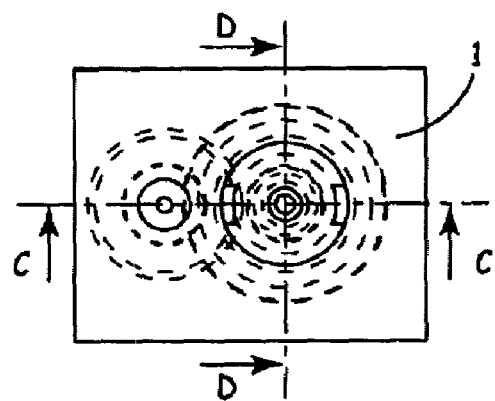

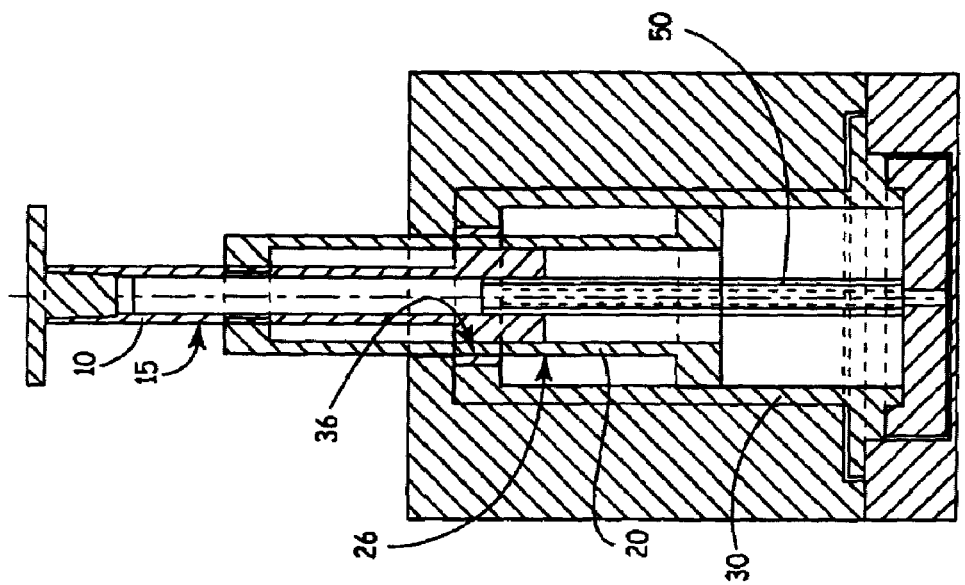
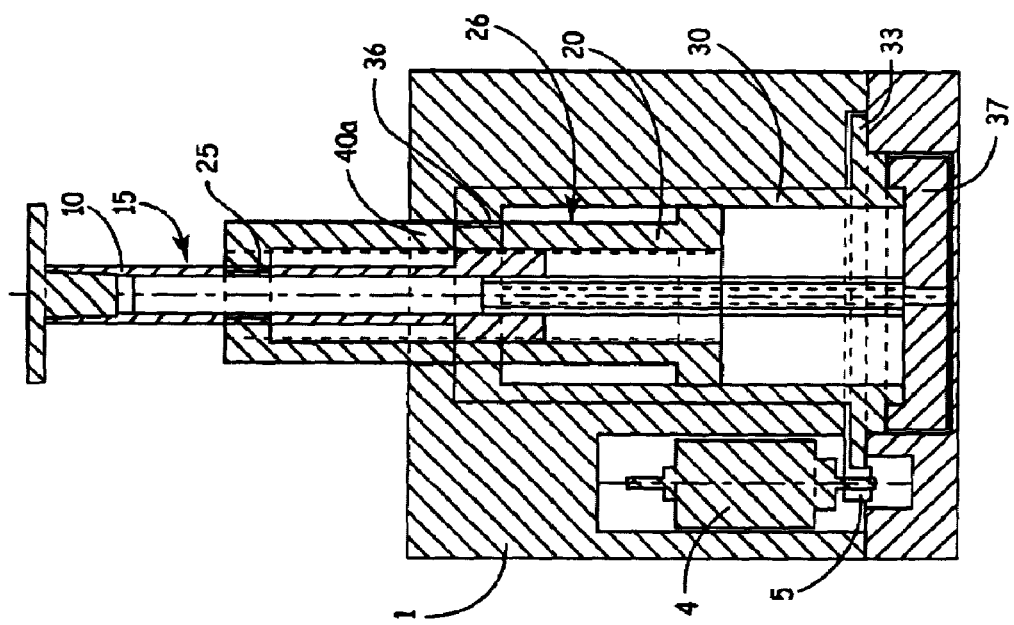

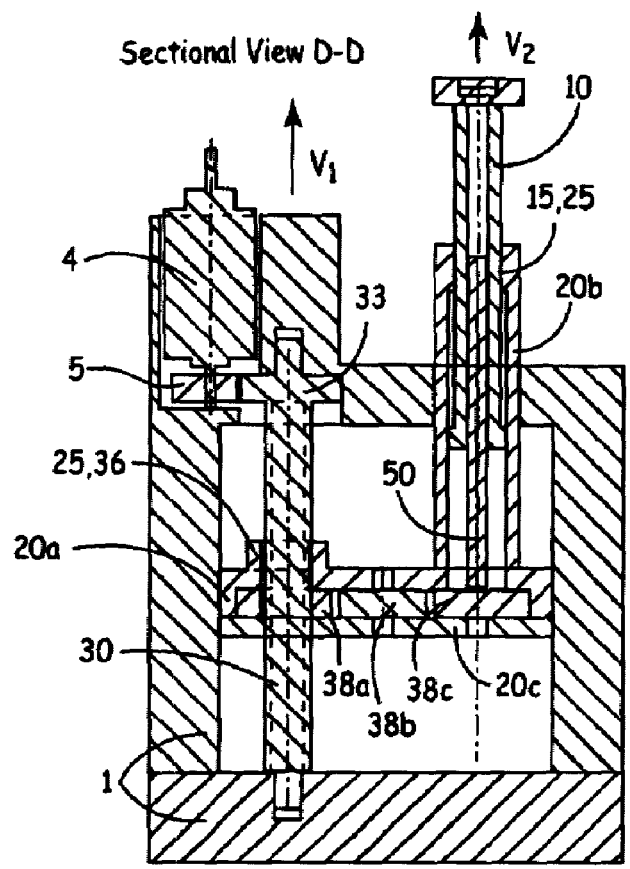
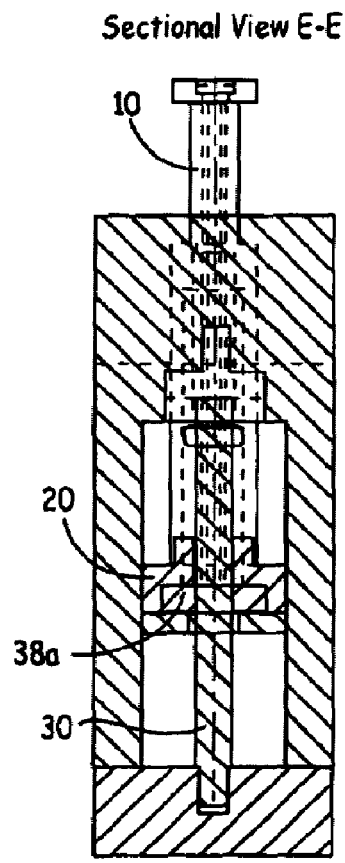
FIG. 20
FIG. 21
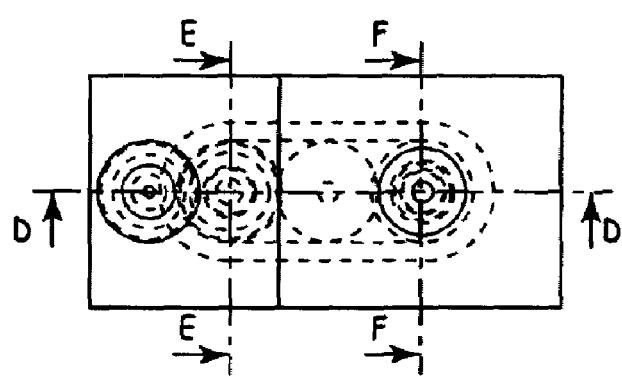
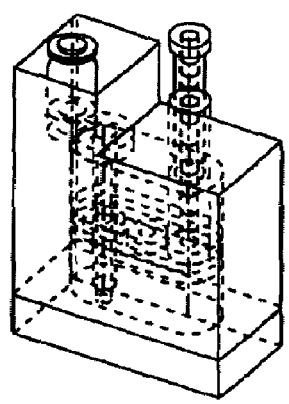
FIG. 19
FIG. 22

PROPELLING DEVICE FOR A PISTON IN A CONTAINER CONTAINING A LIQUID MEDICAMENT

BACKGROUND

The invention relates to a propelling device a piston in a container containing a liquid medicament.

SUMMARY

For administering medicaments in fluid form, more particularly in liquid form, for example insulin, portable injection and/or infusion devices find application. The liquid medicament is dispensed and administered finely metered from a fluid container by means of a piston. These devices find wide application as pumping devices and manually-actuated pens in insulin treatment. An injection pen is known, for example, from WO 93/16740. One example of such a portable infusion device is the H-TRON® plus insulin pump made by Disetronic Medical Systems AG. The user normally carries the device about with him all the time, for example at work or when on vacation. To ensure best possible freedom from an external supply, on the one hand, and freedom of movement, on the other, the device is designed to accommodate as much liquid medicament as possible without being bulky. This requirement for a compact design also exists basically in the medical field; thus also as regards stationary devices and systems.

The object of the invention is to provide a propelling device for a piston in a container containing a liquid medicament which is compact and thus particularly suited as the propelling device for a portable medicament administering device.

This object is achieved by the subject matter of claim 1.

Just like known propelling devices, for example, the H-TRON® plus pump made by Disetronic Medical Systems AG known from EP 0143895 or the injection pen known from WO 93/16740, the propelling device in accordance with the present invention comprises a shifting stage shiftably mounted in or on a base element which, on shifting, advances a piston in a container containing a liquid medicament and thereby medicament from the container. Metering the amount of fluid to be dispensed occurs by setting the path length of the advance movement of the piston at the shifting stage.

In addition to the first shifting stage, at least a second shifting stage is provided which is shiftable in the advance direction of the piston relative to the base element and also relative to the first shifting stage, either manually or motor-driven, and carries the first shifting stage along when shifted in the advance direction of the piston. Due to the multistage operation of the propelling device, the maximum path length by which the piston can be advanced is split up into several increments, namely one increment per shifting stage. The at least two shifting stages are arranged overlapping at least in part in their starting positions. By splitting up the maximum shifting path length into several increments by cascading the propelling device, the overall length of the fluid container and the propelling device, as measured in the advance direction of the piston, is reduced. The shifting stages form preferably a telescopic drive.

Telescopic drives are known from WO 94/15660 and WO 97/00091 which are inserted in a medicament container open at the back end, and are secured to the container, whereby a drive spindle is power-rotated. Two shifting stages, each surrounding the drive spindle, run on and co-axially to the drive spindle. The outer one of these two shifting stages is prevented from rotating, in the case of WO 97/00091, with the aid of an anti-rotation lock to be extended with the outer shifting stage. By rotating the drive spindle, the middle shifting stage running thereon and the outer, non-rotatable shifting stage running on the middle shifting stage are advanced in the container to a container orifice. The piston for dispelling the liquid medicament is secured to the front end of the outer shifting stage.

In accordance with the invention, no fixed connection exists between the container, including piston, and the propelling device, instead the propelling device and the container, including piston, are each separately accommodated in a common housing so that either the container with the piston contained therein or the propelling device or both can be simply exchanged, since a connection of the propelling device to the piston and/or to the container does not first of all have to be released. This facilitates in particular replacing the container, for example, after all its contents have been administered. The propelling device can remain in the housing since it is not involved.

Preferably the propelling device too, is accommodated in the housing for being replaced new. The housing can directly form the cited base element. In a likewise preferred embodiment, the base element forms with the shifting stages accommodated therein and a motor drive, preferably mounted therein, an easily replaceable drive module secured in the housing. The first shifting stage of the propelling device comprises with the piston merely one contacting connection, i.e. it loosely contacts the piston or comes into contact with it only to advance it. The physical separation also renders it, in principle, possible to use the same propelling device for various forms of containers and also in conjunction with various types of pistons.

The shifting stages involved are preferably rigid components, linearly shiftable along one spatial axis only, although, of course, it is just as possible to employ flexible stages to approximate the fluid container.

How the several shifting stages are disposed with respect to each other is dictated by the individual application. Thus, in an arrangement corresponding to one preferred exemplary embodiment, the shifting stages disposed shiftable with respect to the base element are arranged so that their sliding axis, which are simultaneously the longitudinal axes, are in alignment. In its starting position, the one shifting stage thus surrounds the other like a sleeve. Arranging the shifting stages nested also has the advantage of a minimum extension transverse to the advance direction, this being used to advantage in both injection pens and in pumping devices.

If room is available alongside the fluid container, as is the case for example in the H-TRON® plus pump, as already cited, at least one shifting stage may be advantageously arranged there. While the axis, along which the one shifting stage is shifted in the direction of advancement of the piston, is located in the extension of the piston advance direction, the shifting axis of the other shifting stage is distanced parallel thereto.

The shifting stages are shifted preferably by spindle drives with respect to the base element and also relative to each other. Mating of the spindle drive threads is preferably arranged as near as possible to the piston. As a separate spindle drive is used for shifting each shifting stage with respect to the other and, finally, with respect to the base element, a rotational movement initiated, manually or powered, in the propelling device at a point is translated into a continually cumulative shifting movement. Using spindle drives permits one to precisely set the shifting distance. In addition, a spindle drive is also able to carry out the function of a mounting fixture between the individual shifting stages.

In accordance with one example embodiment, one of the two shifting stages is fixedly connected to a rotary drive. The two spindle drives, connected in series, comprise opposing threads. The total distance traveled per rotation of the rotary-driven shifting stage then always equals the sum of the shifting distances traveled by both shifting stages thus coupled. Thus, when thread pitches are the same, for example, a shifting travel is achieved which corresponds to twice the thread pitch of each individual shifting stage.

In accordance with another embodiment of the invention, the threads of two spindle drives connected in series have the same hand. The one shifting stage is advanced by the spindle drive member which rotary drives it or is carried along in the rotational movement. As far as it is shifted, it simply slaves the next shifting stage in its movement. As far as being simply slaved in rotation by the spindle drive member, its own rotational movement generates a forced shifting movement of the subsequent shifting stage prevented from being slaved into rotation by the an anti-rotation lock. This kind of spindle drive cascading permits a particularly precise setting of the shifting travel of the propelling device.

BRIEF DESCRIPTION OF THE DRAWING

Although the invention primarily finds application in portable infusion and/or injection devices it may also be used to advantage in stationary systems.

The invention will now be explained by way of preferred embodiments with reference to the drawings in which:

FIG. 1 is a plan view of a first example embodiment of a propelling device in accordance with the invention, FIG. 2 is a longitudinal section C—C taken through FIG. 1, FIG. 3 is a longitudinal section D—D taken through FIG. 1, FIG. 15 is a longitudinal section through a fourth example embodiment of a propelling device in accordance with the invention, FIG. 16 is another longitudinal section through the propelling device as shown in FIG. 15, FIG. 19 is a plan view of a sixth example embodiment of a propelling device in accordance with the invention, FIG. 20 is a longitudinal section D—D taken through the propelling device as shown in FIG. 19, FIG. 21 is a longitudinal section E—E taken through the propelling device as shown in FIG. 19, FIG. 22 is an overall view in perspective of the propelling device as shown in the FIGS. 19 to 22.

DETAILED DESCRIPTION

Figure 4:
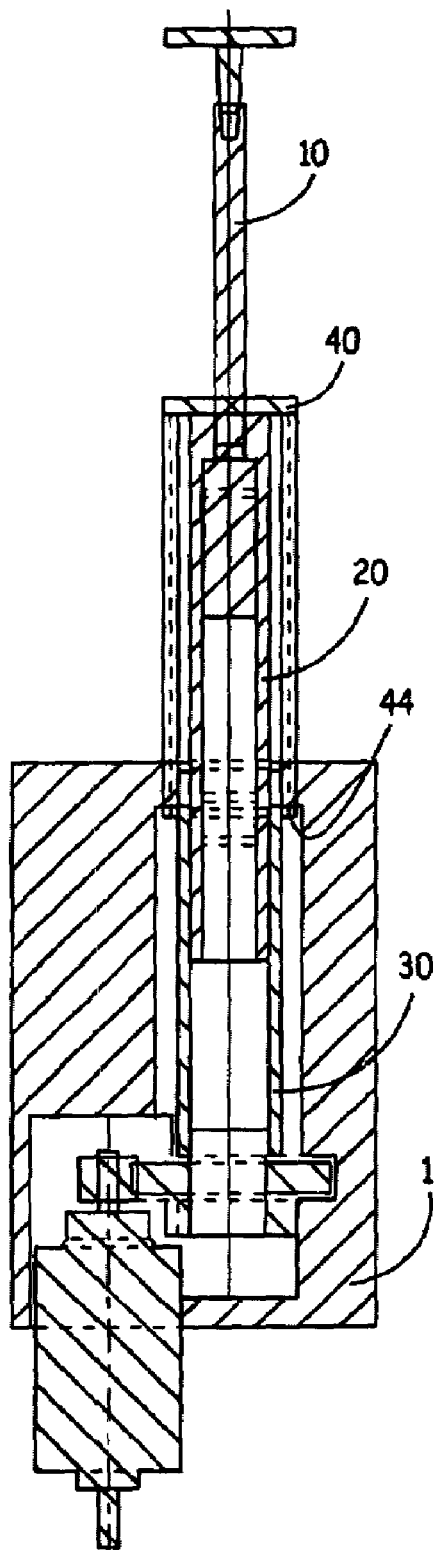
FIG. 4 is the longitudinal section as shown in FIG. 2, but with the propelling device in its fully extended position.

In the plan view of a propelling de shown in FIG. 1, the locations of the longitudinal sections illustrated in FIGS. 2 and 3 are marked.

As its main components, the propelling device comprises a base element 1, two shifting stages 10 and 20, linearly shiftable with respect to the base element 1, an axially fixed rotary drive member 30, rotationally mounted in the base element 1, and a motor 4, rotationally driving the rotary drive member 30. The first shifting stage 10 is configured as a threaded rod with a male thread 15. The second shifting stage 20 is a threaded sleeve having a female thread 25 and a male thread 26. The rotary drive member 30 is likewise cylindrically tubular and will be termed drive sleeve in the following, it comprising a female thread 36 in a head portion and a slaving gearwheel 22 in a footing portion.

The slaving gearwheel 33 meshes with a gearwheel 5 located on the shaft of the motor 4. The threaded rod 10 and the threaded sleeve 20 form by their threads 15 and 25 a first spindle drive. The threaded sleeve 20 and the drive sleeve 30 form by their threads 26 and 36 a second spindle drive. The two sleeves 20 and 30 surround the threaded rod 10 concentrically about a common longitudinal centerline simultaneously pointing in the advance direction of the propelling device. In this advance direction, the propelling device, in itself being advanced, advances a piston accommodated in a reservoir or container containing a liquid medicament, for example in the form of a prefabricated syringe body, by the threaded rod 10, as the most proximal or first shifting stage advancing the piston by means of a proximal flange 11 urging the piston in the direction of the orifice of the container to thus dispel fluid from the container. In this arrangement, the base element 1 locates the propelling device with respect to the container. The base element 1 may be secured to a frame or in a housing, or itself form the frame or housing.

In the base element 1, the drive sleeve 30 is rotatively mounted, as well as located axially and radially, in a bearing position 3a, preferably a plain bearing for rotation about the longitudinal centerline of the propelling device, simultaneously forming the axis of rotation thereof. A radial bearing position 3b for the drive sleeve 30 is located in the upper portion of the base element 1. The threaded sleeve 20 is supported in the drive sleeve 30 by the second spindle drive formed between the threads 26 and 36, i.e. the threaded sleeve 20 is shiftable via the second spindle drive with respect to the drive sleeve 30 and is also freely rotatable in the second spindle drive.

The threaded rod 10 is prevented from rotating with respect to the base element 1. This anti-rotation lock is achieved by means of an anti-rotation fork 40, which is linearly shiftable with respect to the threaded rod 10, but is not rotatable and which itself is locked against rotating in the base element 1, and is slidingly guided along the longitudinal centerline of the propelling device.

Advancement of the threaded rod 10 thus occurs as follows:

The rotative movement of the motor is transmitted via the spur reduction gearing 5, 33 to the drive sleeve 30. The rotative movement of the drive sleeve 30 is transmitted via the second spindle drive formed between the threads 36 and 26 to the threaded sleeve 20. Depending on the frictional forces acting on the threaded sleeve 20, the threaded sleeve 20 is either slaved in the rotative movement or advanced along its axis of rotation by the spindle drive comprising the threads 26, 36. The movement of the threaded sleeve 20 may also be a compounded telescoping/rotative movement. When only shifting of the threaded sleeve 20 is involved, it simply slaves the threaded rod 10 in this movement. When compounded slave rotation of the threaded sleeve 20 is involved, the rotative movement of the threaded sleeve 20 produces via the second spindle drive formed by the threads 15 and 25 an advance movement of the threaded rod 10 with respect to the threaded sleeve 20 due to the anti-rotation lock of the threaded rod 10. To achieve this movement characteristic, the threads 26 and 15, i.e. the threads via which each of the two shifting stages 10 and 20 are driven have the same hand.

Referring now to FIGS. 2 and 3, the propelling device is illustrated in a position in which it is partly extended from a starting position in the base element 1. In the starting position, the two nested shifting stages 10 and 20 are accommodated in a cavity of the base element 1. In this starting position, each of the two shifting stages 10 and 20 is in contact with the bottom of the cavity by its rear face contacting a bottoming surface area 2.

Figure 5:
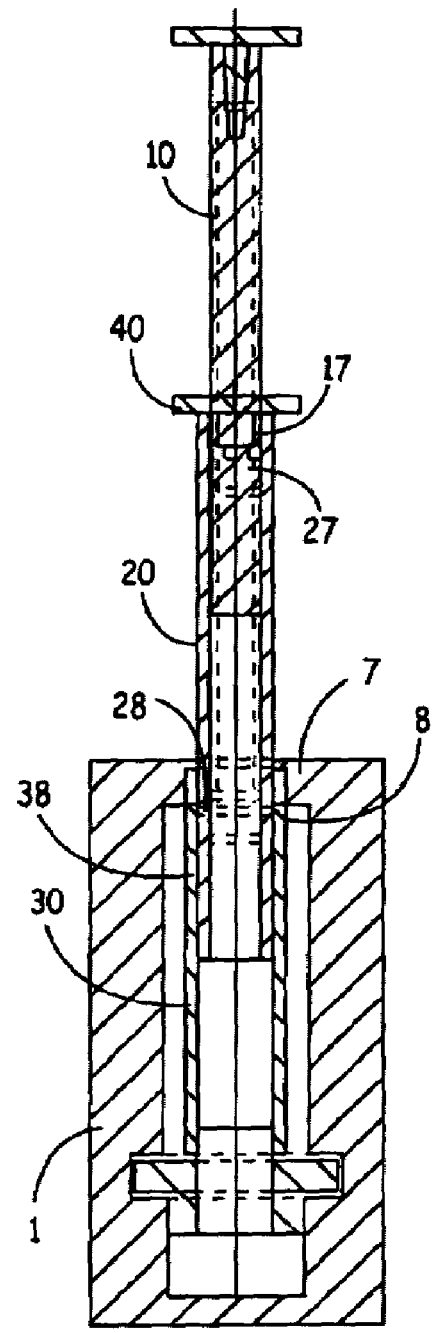
FIG. 5 is the longitudinal section as shown in FIG. 3, but with the propelling device in its fully extended position.
Figure 6:
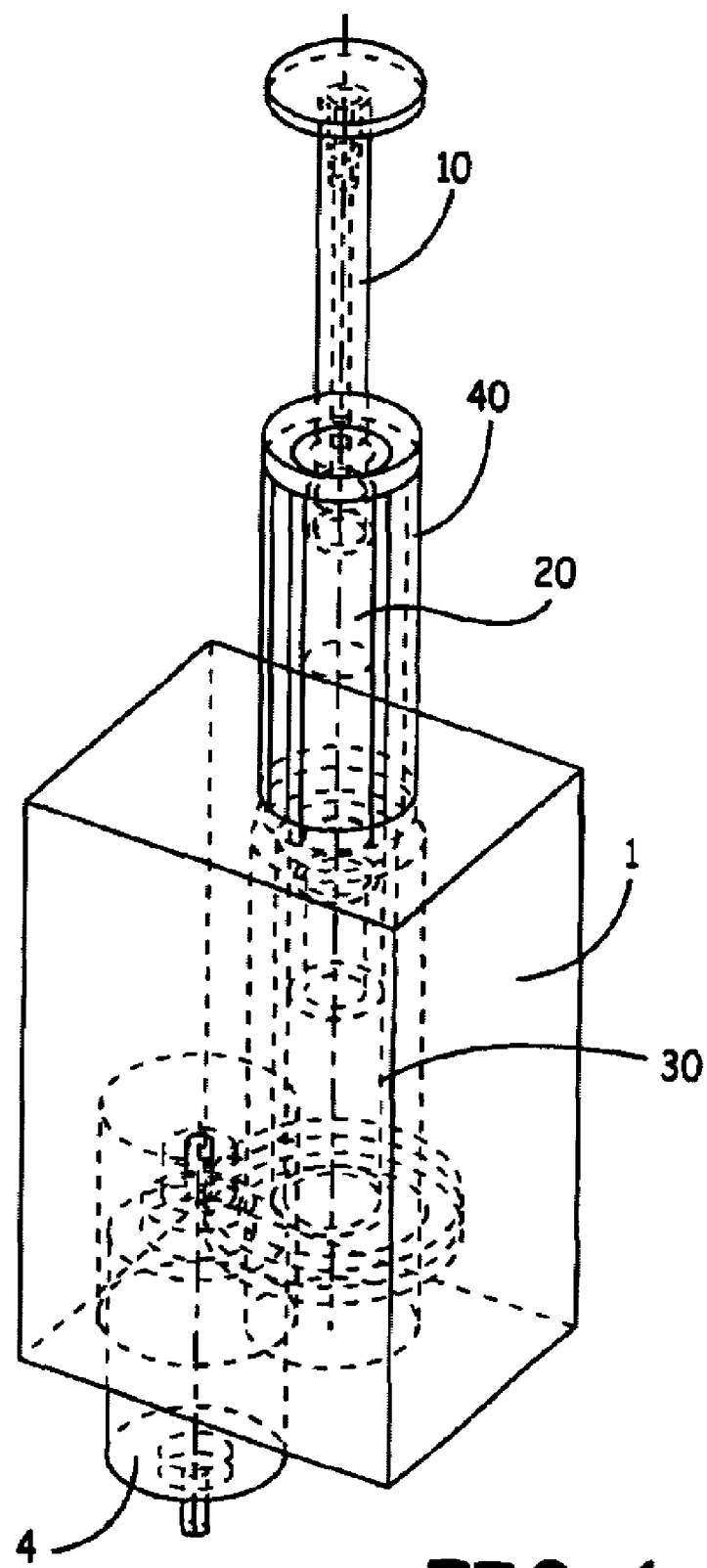
FIG. 6 is an overall view in perspective of the propelling device as shown in FIGS. 1–5

Referring now to FIGS. 4 and 5, illustrated is the propelling device in the same sections as shown in FIGS. 2 and 3, but here in the fully extended position. In this position, the propelling device is also illustrated in an overall view in perspective in FIG. 6.

The proximal end position of the threaded rod 10 in the threaded sleeve 20 is dictated by a pair of stops 17, 27 and the most proximal end position of the threaded sleeve 20 in the drive sleeve 30 is dictated by a pair of stops 28, 38 (FIG. 5). Each of the stops 27 and 38 is formed as a circumferential shoulder protruding radially inwards from the inner circumferential surface areas of the nut/sleeve 20 and 30 respectively, whilst the corresponding counter-stops 17 and 27 are formed by thickened annular portions of the threaded rod 10 and threaded sleeve 20 respectively.

A third pair of stops 8, 44 prevents the anti-rotation fork 40 from dropping out of the propelling device. The fork 40 may also be fixed to the threaded sleeve 20. The stop 8 is formed by shoulders 7 protruding inwards in the direction of the shifting axis at the proximal end of the cavity of the base element 1. The anti-rotation fork 40 comprises at its distal end corresponding, counterhook-type protuberances 44, jutting radially outwards.

Figure 7:
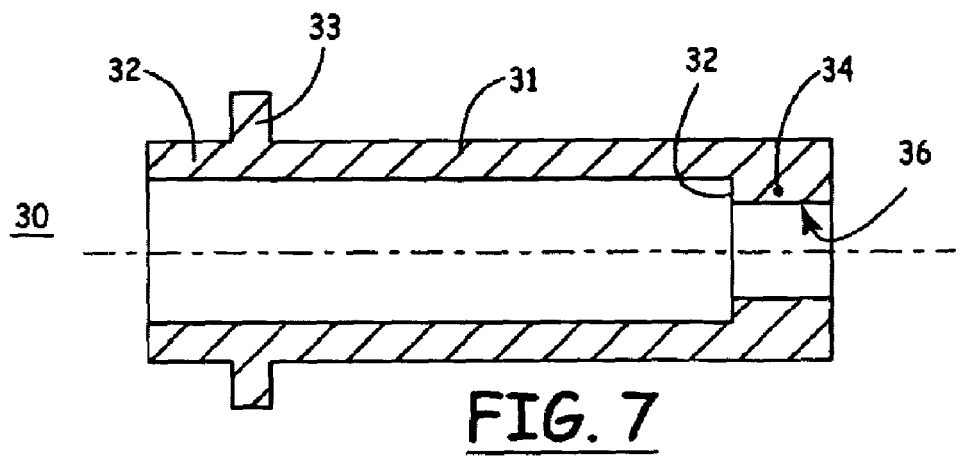
FIG. 7 is an illustration of the drive sleeve of the propelling device as shown in FIGS. 1 to 6.

Referring now to FIG. 7, it illustrates a longitudinal section of the drive sleeve 30. This essentially comprises a simple cylindrically-tubular base body 31, configured thickened in the footing portion 32 in order for better guidance of the drive sleeve 30, so that the outer shell surface area of the footing portion 32 slides in the right cylindrical cavity of the base element 1 on rotation of the drive sleeve 30, and represents an additional means of radially stabilizing the system with respect to the bearing 3. The slaving gearwheel 33 is a simple spur gear formed by a gear shoulder radially surrounding the shell surface area of the drive sleeve 30. At its proximal end, the drive sleeve 30 is provided within a shoulder portion 34 protruding radially inwards with a thread 36, which may be a fine thread, a multiple coarse pitch thread or even a regulating thread. The face 38 of the shoulder portion 34, facing the footing portion 32, forms the stop for the threaded sleeve 20.

Figure 8:
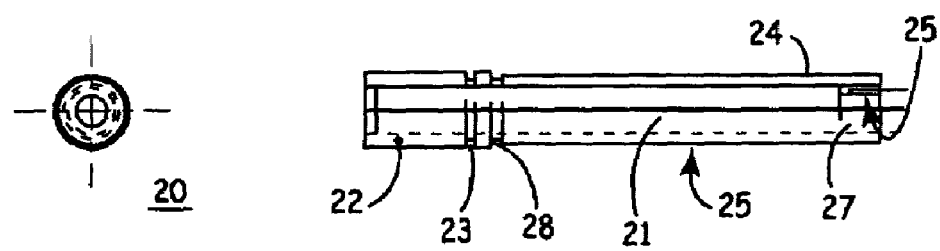
FIG. 8 is an illustration of the feed nut of the propelling device as shown in FIGS. 1 to 6.

Referring now to FIG. 8, illustrated is the threaded sleeve 20 which likewise essentially comprises a simple cylindrically-tubular base body 21. Starting from the most proximal end of the base body 21, the threaded sleeve 20 is provided over by far the majority of its length with a thread 26 which runs in the thread 36 of the drive sleeve 30. The distal portion 22 of the threaded sleeve 20 is a simple annular cylinder, the outer diameter of which is somewhat larger than the outer diameter of the portion having the thread 26. Due to this thickening, the counter-stop 28 is formed for the stop 38 of the drive sleeve 30. The footing portion 22 is slide-guided in the drive sleeve 30, it featuring furthermore a circumferential recess at 23, this recess 23 serving to seat a sealing ring. At the proximal end, the threaded sleeve 20 comprises a shoulder portion 24 protruding radially inwards. In the shoulder portion 24, the thread 35 is configured (the same applying to it as what was said about thread 36). The face of the shoulder 24 facing the footing portion 22 serves as the stop 27 for the threaded rod 10.

Figure 9:
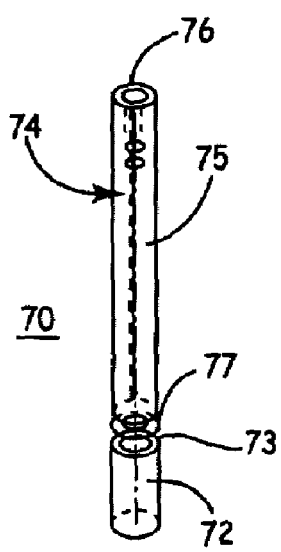
FIG. 9 is an illustration of the feed screw of the propelling device as shown in FIGS. 1 to 6.

FIG. 9 illustrates the threaded rod 10, likewise formed by a right cylindrical base body. A simple right cylindrical footing portion 12 is itself slightly thickened with respect to the substantially longer threaded portion, the footing portion 12 also serving as a sliding guide in shifting the threaded rod 10 in the threaded sleeve 20. Seated in a circumferential annular container 13 in the footing portion 12 is a sealing ring in the fitted condition. The portion with the thread 15 has two opposing flats 14. At its proximal end, the threaded rod 10 is faced with a blind hole 16 to which the flange 11 is bolted. In cooperation with the anti-rotation fork 40, the flat 34 prevents the threaded rod 10 rotating with respect to the base element 1.

Figure 10:
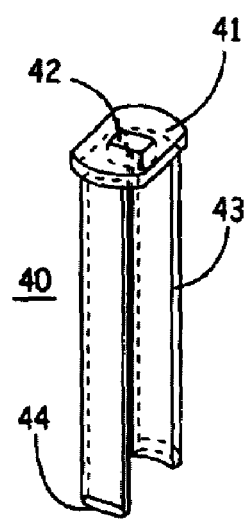
FIG. 10 is an illustration of the anti-rotation lock of the propelling device as shown in FIGS. 1 to 6.

FIG. 10 shows finally the anti-rotation fork 40. It is a sleeve open at one end and closed off at the other end by a disk 41, the sleeve being provided with slots over its entire length, two slots being evident in the example embodiment, owing to which or to the strip-shaped longitudinal receiving portions it has the form of two-pronged fork. The disk 41 is provided with a port 42 which is penetrated by the threaded rod 10 in the fitted condition. This port 42 is defined by two circumferential flats joined by the annular cylinder surface areas. The threaded rod 10 is thus axially slide-guided in the region of its thread 15 and of its two guide flats 14 in the port 42 but is prevented from rotating relative thereto by the anti-rotation fork 40. The two axial projections 43 are snugly slide-guided in the base element 1 so that the anti-rotation fork 40 is itself unable to rotate with respect to the base element 1, it instead merely permitted a longitudinal sliding action. It is in this way that rotation of the threaded rod 10 with respect to the base element 1 is prevented. As already mentioned, counterhook-shaped projections 44 at the distal end of the anti-rotation fork 40 prevent the anti-rotation fork 40 from dropping out of the base element 1.

Referring now to FIGS. 11 to 18, shown are four alternative example embodiments of propelling devices in accordance with the invention. In these examples too, as in the first example embodiment, the straight lines, along which the shifting stages 10 and 20 are telescoped, are in alignment. FIGS. 19 to 22 show a sixth example embodiment in which the first and the second shifting stages are shifted on straight lines distances parallel to each other. In the following, components comparable to those of the first example embodiment are assigned the same reference numerals since they fulfill the same function as those of the former. Reference is always made to the detailed explanations of the first example embodiment in supplementing the following description.

Unlike in the first example embodiment, in the following example embodiments to be described no free rotation of a shifting stage is permitted.

Each rotational movement introduced by a shifting stage is inevitably translated into a corresponding shifting movement of this shifting stage.

Figure 11:
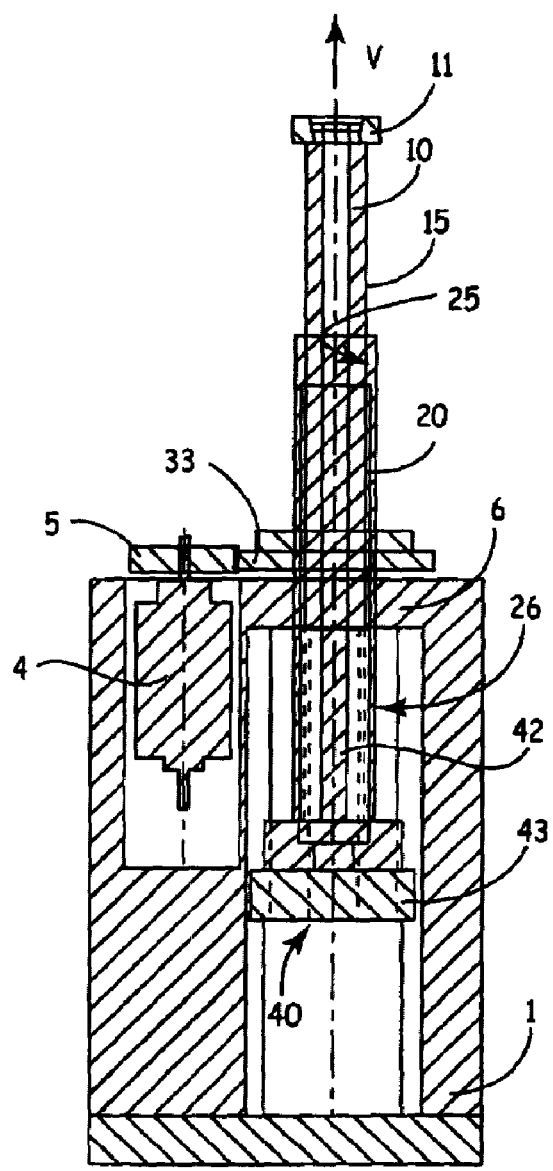
FIG. 11 is a longitudinal section through a second example embodiment of a propelling device in accordance with the invention.
Figure 12:
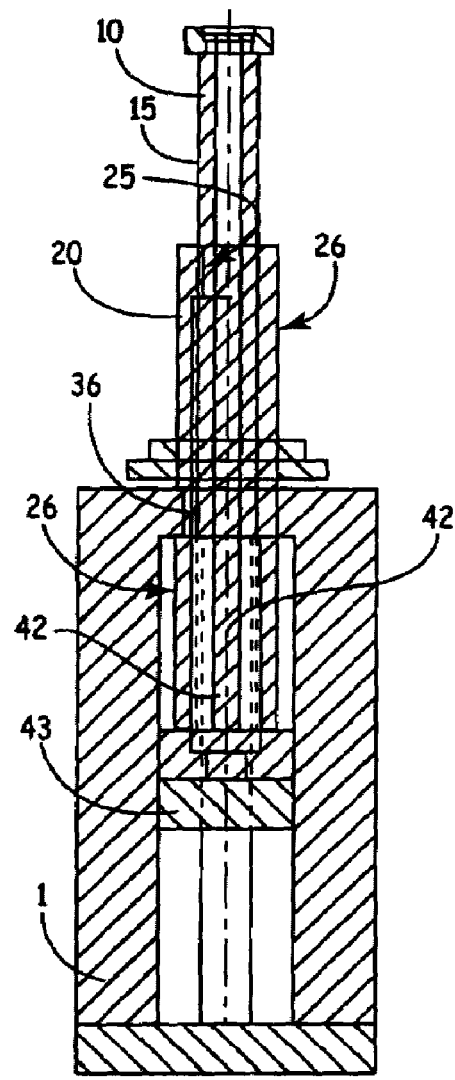
FIG. 12 is another longitudinal section through the propelling device as shown in FIG. 11.

In the example embodiment of FIGS. 11 and 12, the rotational movement of the motor 4 is transmitted via the rim gear 5, 33 directly to the threaded sleeve 20, "direct" in this context meaning that rotation of the slaving gearwheel 33 with respect to the threaded sleeve 20 is not possible. The threaded sleeve 20 is shifted closely slide-guided in a longitudinal direction in the slaving gearwheel 33 non-rotationally. In this example embodiment, the threaded rod 10 is formed cylindrically-tubular with a circumferential male thread 15 and an inner circumferential surface area in which an anti-rotation lock 40 is slide-guided. Via their threads, the threaded rod 10 and the threaded sleeve 20 form—as in the first example embodiment—a first spindle drive. The second spindle drive is formed by the threaded sleeve 20 and the base element 1, said base element being provided with a thread 36 in a proximal shoulder portion 6 protruding radially inwards in the direction of the threaded sleeve 20. Via the threads 26 and 36, the threaded sleeve 20 and the shoulder portion 6 of the base element 1 form the second spindle drive. As viewed cross-sectionally, the threaded sleeve 20 forms a circular ring with two outer flats for the longitudinal guidance, and the thread 26 on the two circular segment sides for the rotary drive by the slaving gearwheel 33.

In the example embodiment as shown in FIGS. 11 and 12, the anti-rotation lock 40 is guided in the inner cavity of the threaded rod 10 and prevents its rotation with respect to the base element. The anti-rotation lock 40 comprises a footing portion 43 which is slide-guided in the base element locked against rotating. Protruding from the footing portion 43 is a guide rod 42 which totally passes through the threaded rod 10 in the starting position of the propelling device. The guide rod 42 is formed so that it prevents rotation of the first shifting stage 10 with respect to the base element whilst permitting shifting. The second shifting stage 20 is seated on the footing portion 43 of the anti-rotation lock 40, connected thereto so that it is freely rotational with respect to the footing portion 43, on the one hand, but slaving the anti-rotation lock 40 in its own shifting movement, on the other, thus including the first shifting stage 10 in the shifting movement.

The rotation of the threaded sleeve 20 slaved by the slaving gearwheel 33 results in the threaded sleeve 20 being shifted by means of the second spindle drive in the advance direction V or in the opposite direction, the base element 1 acting as the direct reaction member of the second spindle drive, i.e. the threaded sleeve 20 is simultaneously the drive member and driven member of the second spindle drive. It is furthermore also the drive member of the first spindle drive, the driven member of which is the threaded sleeve 10. The thread 26 leading to shifting of the threaded sleeve 20 and the corresponding thread 15 of the threaded sleeve 10 have the opposite hand. Every rotational movement of the threaded sleeve 20 always produces shifting of the threaded sleeve 10 due to a relative rotation.

Figure 13:
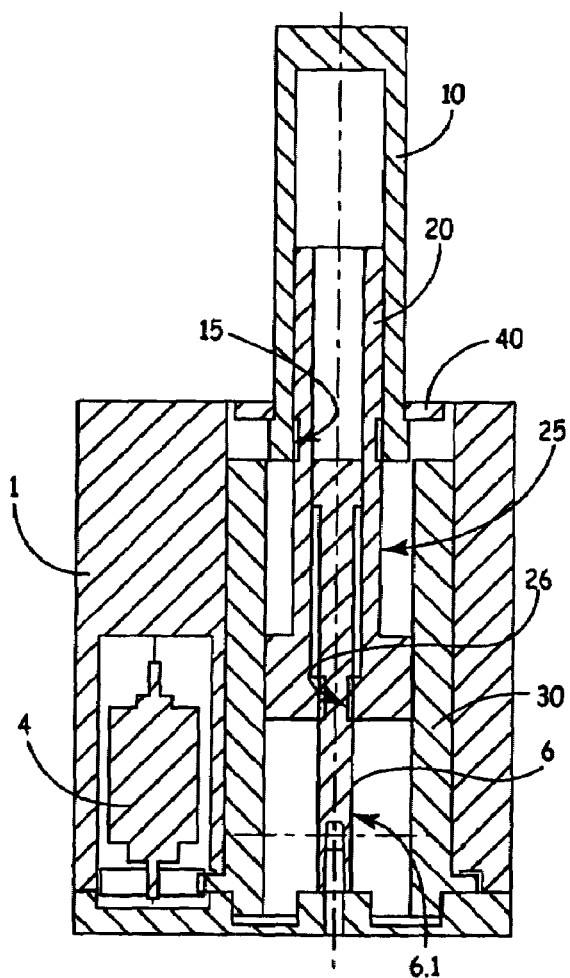
FIG. 13 is a longitudinal section through a third example embodiment of a propelling device in accordance with the invention.
Figure 14:
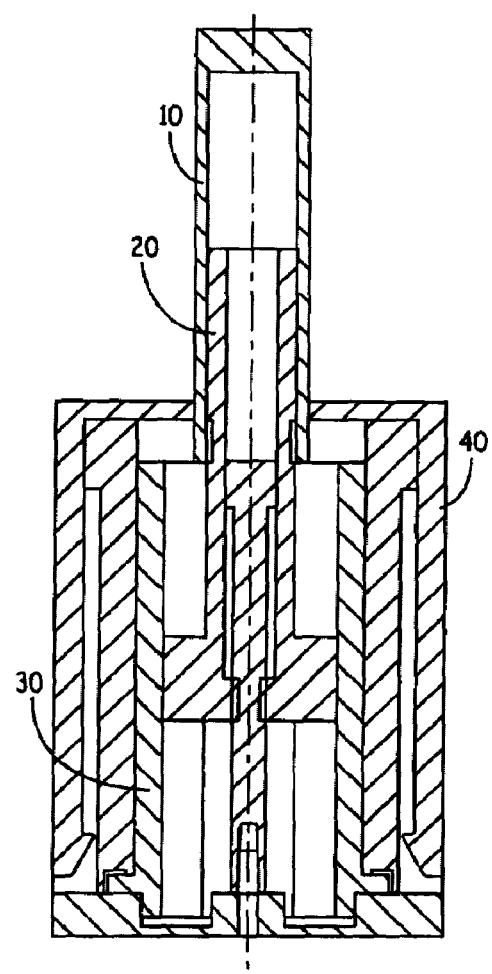
FIG. 14 is another longitudinal section through the propelling device as shown in FIG. 13.

FIGS. 13 and 14 illustrate a propelling device which functions comparable to that as shown in FIGS. 11 and 12. As regards the matching features, reference is made more particularly to the latter, but always supplementary to the explanations of the first example embodiment.

The propelling device as shown in FIGS. 13 and 14 comprises likewise two spindle drives. However, in this example embodiment, the first shifting stage 10 nests the second shifting stage 20 although still termed a feed screw. The first spindle drive is formed by a female thread 15 of the threaded rod 10 and a corresponding male thread of the threaded sleeve 20. An anti-rotation lock 40 prevents rotation of the threaded rod 10 with respect to the base element 1. The anti-rotation lock 40 is comparable to the anti-rotation fork of the first example embodiment. The rotary drive of the threaded sleeve 20 is achieved by means of an axially fixed drive sleeve 30, rotationally mounted in the base element 1. In its footing portion, this drive sleeve 30 is rigidly connected to a slaving gearwheel which meshes with a gearwheel on the shaft of the motor 4. The threaded sleeve 20 is prevented from rotating in the drive sleeve 30, resulting in a transfer of the rotational movement from the drive sleeve 30 to the threaded sleeve 20 while permitting longitudinal slide-guided shifting. The drive sleeve 30 is furthermore centrally penetrated by a feed screw 6. The feed screw 6 is rigidly connected to the base element 1. In this way, the rotational movement of the drive sleeve 30 is translated into a rotational movement of the threaded sleeve 20 and by means of the feed screw 6 into a shifting movement of the threaded sleeve 20.

Referring now to FIGS. 15 and 16, illustrated is a further propelling device in which, however, the threaded rod 10 is directly driven in rotation and the threaded sleeve 20 is prevented from any rotation with respect to the base element 1. The rotary drive of the drive sleeve 30 occurs like in the example shown in FIGS. 13 and 14, except that within the drive sleeve 30 a rod-shaped rotary drive member 50 is provided non-rotationally connected thereto for the first threaded rod 10. This rotary drive/slaving rod 50 protrudes from a cover secured to the distal face end of the drive sleeve 30 in the advance direction and into the threaded rod 10. The rotary drive rod 50 is configured itself multi-stage, i.e. in the example embodiment two-stage corresponding to the number of movable shifting stages—like a telescope—following extension of the threaded rod 10. The threaded sleeve 20 is prevented from rotating with respect to the base element 1 by an anti-rotation lock 40a provided as sliding surface area directly on the base element 1. This is why any rotation of the drive sleeve 30 is always translated into a shifting movement of the threaded sleeve 20. Due to the non-rotational connection, any rotation of the drive sleeve 30 results in the same rotation of the rotary drive rod 50 and thus of the threaded sleeve 10.

Figure 17:
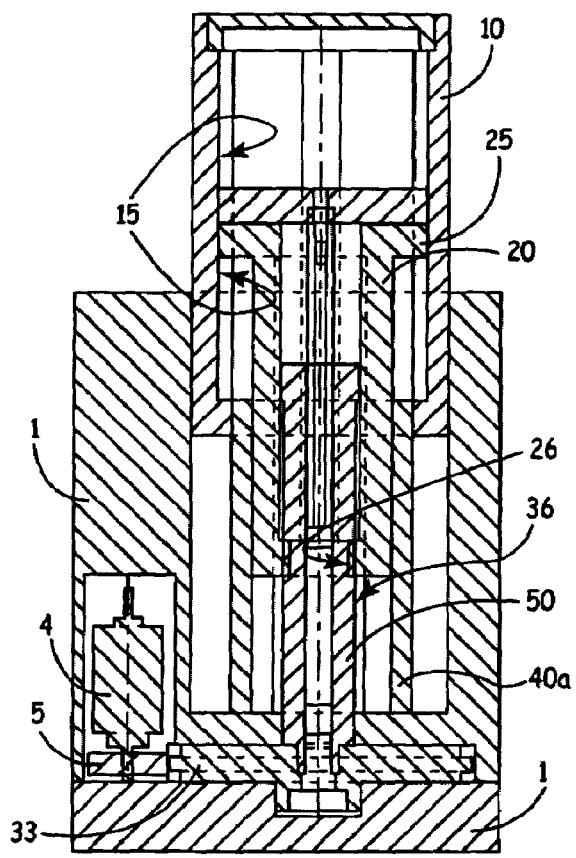
FIG. 17 is a longitudinal section through a fifth example embodiment of a propelling device in accordance with the invention.
Figure 18:
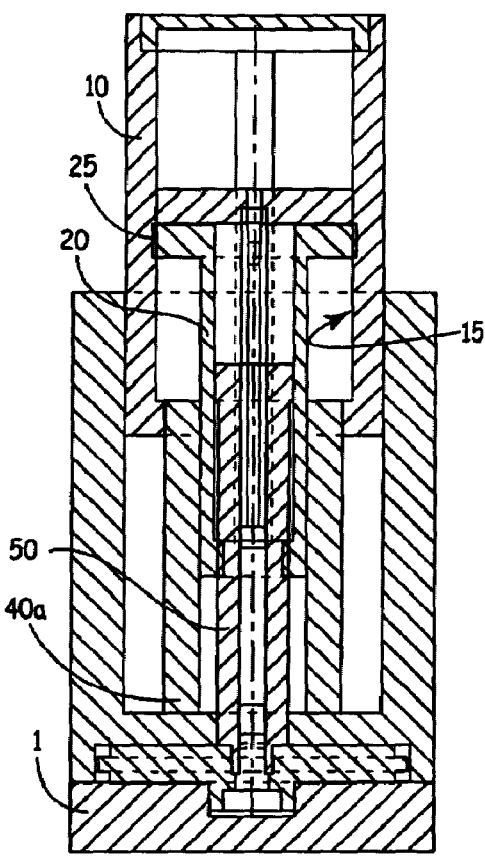
FIG. 18 is another longitudinal section through the propelling device as shown in FIG. 17.

The example embodiment shown in FIGS. 17 and 18 substantially corresponds to that as of FIGS. 15 and 16, the differences in design being already apparent from FIGS. 17 and 18.

FIGS. 19 to 22 illustrate a sixth example embodiment. In this example embodiment, the first and second shifting stages are moved along two straight lines parallel to each other, i.e. the shifting axles of the first and the second spindle drives are spaced away parallel to each other. Included in the plan view in FIG. 19 are the locations of the two longitudinal sections shown in FIGS. 20 and 21.

Also in this sixth example embodiment, components having the same functions as those of previous example embodiments are given the same reference numerals.

Advancement of the most-proximal first shifting stage 10 is again achieved by a rotary drive of a drive stage 30 which in this example embodiment is devised as a simple spindle. The spindle 30 is rotationally mounted in the base element 1, but prevented from any other movement with respect to the base element 1. The axis of rotation of the spindle 30 runs in the advance direction V1 and V2 of the shifting stages 10 and 20. The spindle 30 is itself rotary driven by a motor 4 via spur gears 5, 33. Seated on the spindle 30 is a first sleeve body 20a of the second shifting stage 20. The second shifting stage 20 is U-shaped. The sleeve body 20a forms one leg of the U and a second sleeve body 20b, spaced away from the other parallel thereto, forms the other leg of the U. The two sleeve bodies 20a and 20b protrude perpendicularly from a connecting web 20c, said sleeve bodies forming therewith as the cover a housing of the second shifting stage 20. In the base element 1, the sleeve body 20a and the connecting web 20c are movably slide-guided along the axis of rotation of the spindle 30, and prevented from rotating. In the second sleeve body 20b, the first shifting stage 10, again configured as a feed screw, is shifted in and contrary to the advance direction of the piston and shiftingly rotated around, the longitudinal centerline of the second sleeve body 20b which coincides with its own longitudinal centerline.

Rotation of the spindle 30 causes the second shifting stage 20 to be forcibly shifted along the axis of rotation of the spindle via the pairing of the threads 26, 36. Seated on the spindle 30, non-rotationally with respect to the spindle 30 but axially shiftable, is a spur gear 38a. Slide-guiding and non-rotational shifting is formed by flats on the circumference of the spindle 30 and corresponding companion flats on the spur gear 38a. The spur gear 38a is accommodated in the housing 20a–c of the second shifting stage 20 so that it is slaved in the shifting movement of the latter while being freely rotational with respect to the housing of the shifting stage 20. Rotationally mounted in the housing of the shifting stage 20 are, furthermore, a second gearwheel 38b meshing with the spur gear 38a as well as a third spur gear 38c meshing with the spur gear 38b. The three gearwheels 38a, 38b and 38c form a spur gear unit for rotary drive of a slaving rod 50, protruding perpendicularly from the gearwheel 38c, for the threaded rod 10. The slaving rod 50 protrudes into the cylindrically-tubular threaded rod 10 and is non-rotationally slide-guided. It slaves the threaded rod 10 in its own rotation compulsorily and with zero clearance. Like in the aforementioned example embodiments, rotation of the threaded rod 10 is translated into a shifting movement of the threaded rod 10 by means of a first spindle drive formed by the pairing of the threads 15, 25.

Figure 23:
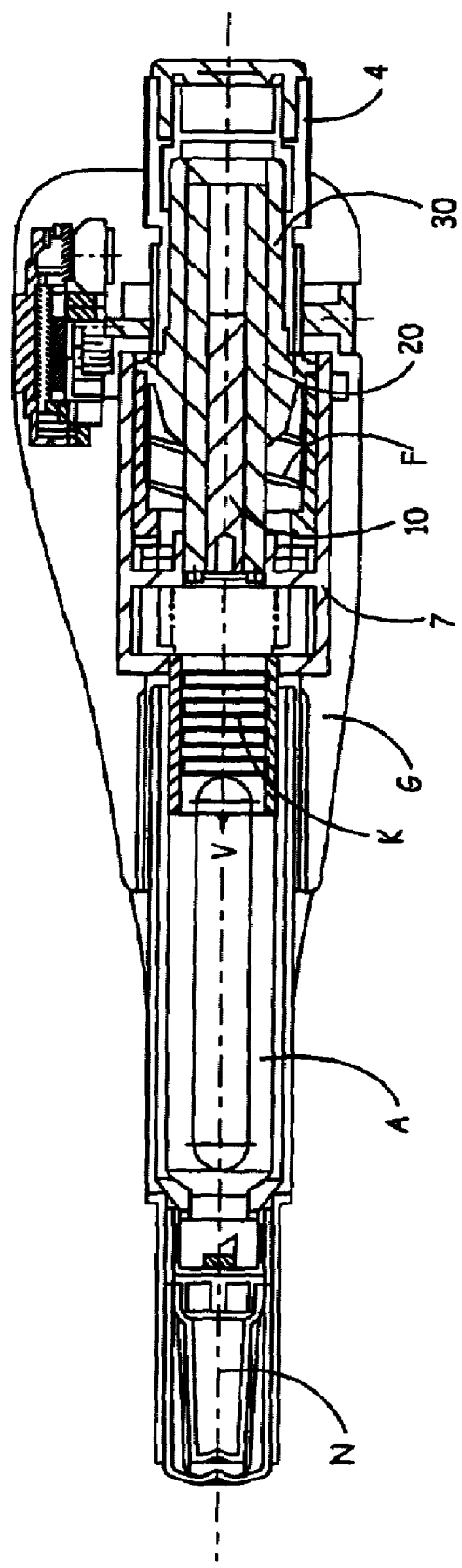
FIG. 23 is an illustration of an injection device including a propelling device in accordance with the invention

FIG. 23 shows a so-called pen as used in particular for insulin injection. Accommodated in the housing G of the injection pen is a syringe body A comprising a piston K and containing a liquid medicament. The piston is shiftable in the direction of a syringe body orifice in an advance direction V, dispelling on its advancement a precisely metered amount of fluid from the syringe body A via a needle hub into and through a needle N. The piston K is held in the syringe body A, i.e. it is removed together with the syringe body A and may be replaced by a new syringe body with a new piston. The base element 1 serves, together with a dispensing and actuator knob 4, to mount the propelling device, is accommodated independent of the container A in the housing G, and is fixed in its position relative to the container A and the piston K. However, with its proximal edge, the base element 1 serves to locate the syringe body A. Accordingly, screwing open the housing G results in a proximal and a distal housing sleeve, the syringe body A being accommodated in the proximal housing half and the propelling device in the distal housing half. When screwed together, the base element 1 is forced against the distal edge of the syringe body so as to seat the syringe body A non-shiftable in a longitudinal direction in the housing G.

Advancement of the piston K is caused by extension of a threaded rod 10 which, on being extended, urges against the distal end of the piston to advance the piston K in the syringe body A. The threaded rod 10 forms the first shifting stage of a telescopic drive. The second shifting stage is formed by a threaded sleeve 20 in which the threaded rod 10 runs by means of a first spindle drive. The threaded sleeve 20 is itself nested in a drive sleeve 30 with which it forms a second spindle drive for extending and retracting it in and against the advance direction V. The drive sleeve 30 is rotationally mounted in the housing 1. The drive sleeve 30 is manually turned with respect to the housing G by means of the dispensing and actuator knob 4 around the longitudinal centerline of the propelling device 10, 20, 30, pointing in the advance direction V, for setting the dose of insulin to be administered, and is then advanced together with the threaded rod 10 and the threaded sleeve 20 along the longitudinal axis. After injection or after actuation of a reset knob, the feed nut is then returned into its starting position ready for the next injection, due to a spring F thereby being compressed.

Dispensing and manually actuating the injection pen occurs as in known pens, reference being made in this respect, for example, to the description of such an injection pen in WO 93/16740. However, contrary to known injection pens, a propelling device in accordance with the invention is used for the piston K of the pen as shown in FIG. 23. The propelling device of this example application corresponding the first example embodiment.

Figure 24:
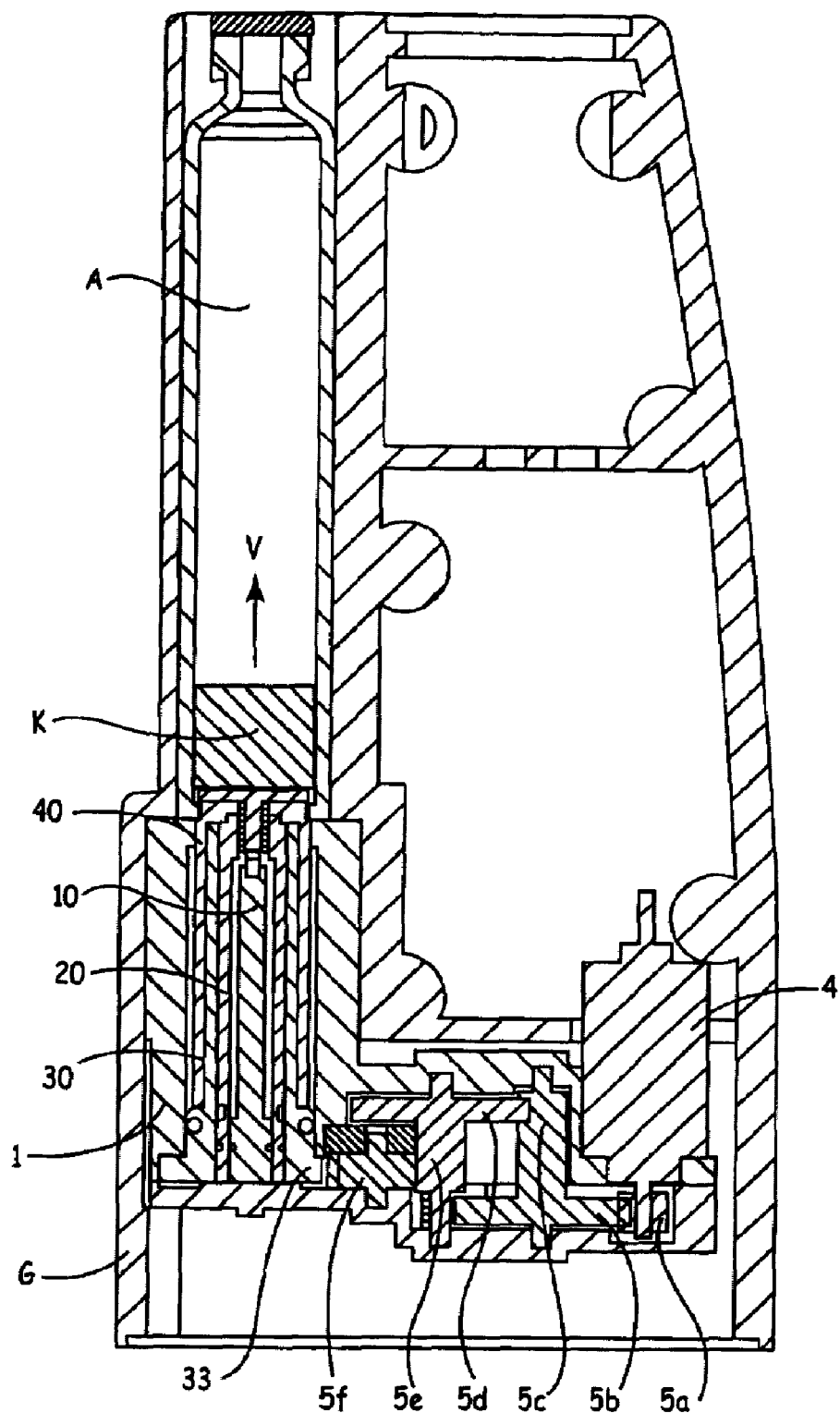
FIG. 24 is an illustration of an infusion device including a propelling device in accordance with the invention

FIG. 24 illustrates a portable infusion device, more particularly for insulin treatment, including a motor-powered propelling device, for instance, the propelling device as shown in the FIGS. 1 to 10. The base element 1—including the drive sleeve 30, two shifting stages 10 and 20 and the anti-rotation fork 40—is fixed in place in the pump housing G by, among other things, being mutually shaped accordingly.

To facilitate its replacement, the syringe body A including the piston K retained therein can be simply inserted in and removed from the housing G in the example as shown in FIG. 23. In other words, free of any connection first needing to be released. When replacing the syringe body A, the propelling device can remain in the housing G or be replaced independent of the syringe body A. However, as already discussed with reference to the example embodiment as shown in FIG. 23, the base element 1 serves as a stopper, i.e. for locating the syringe body A lengthwise. The syringe body A can be moved to and fro in an insertion shaft of the housing G until this stop, it thereby being guided lengthwise. After insertion, it is locked in place to prevent it from being advanced in the shaft by means of the locking means to be secured to the housing G.

Figure 25:
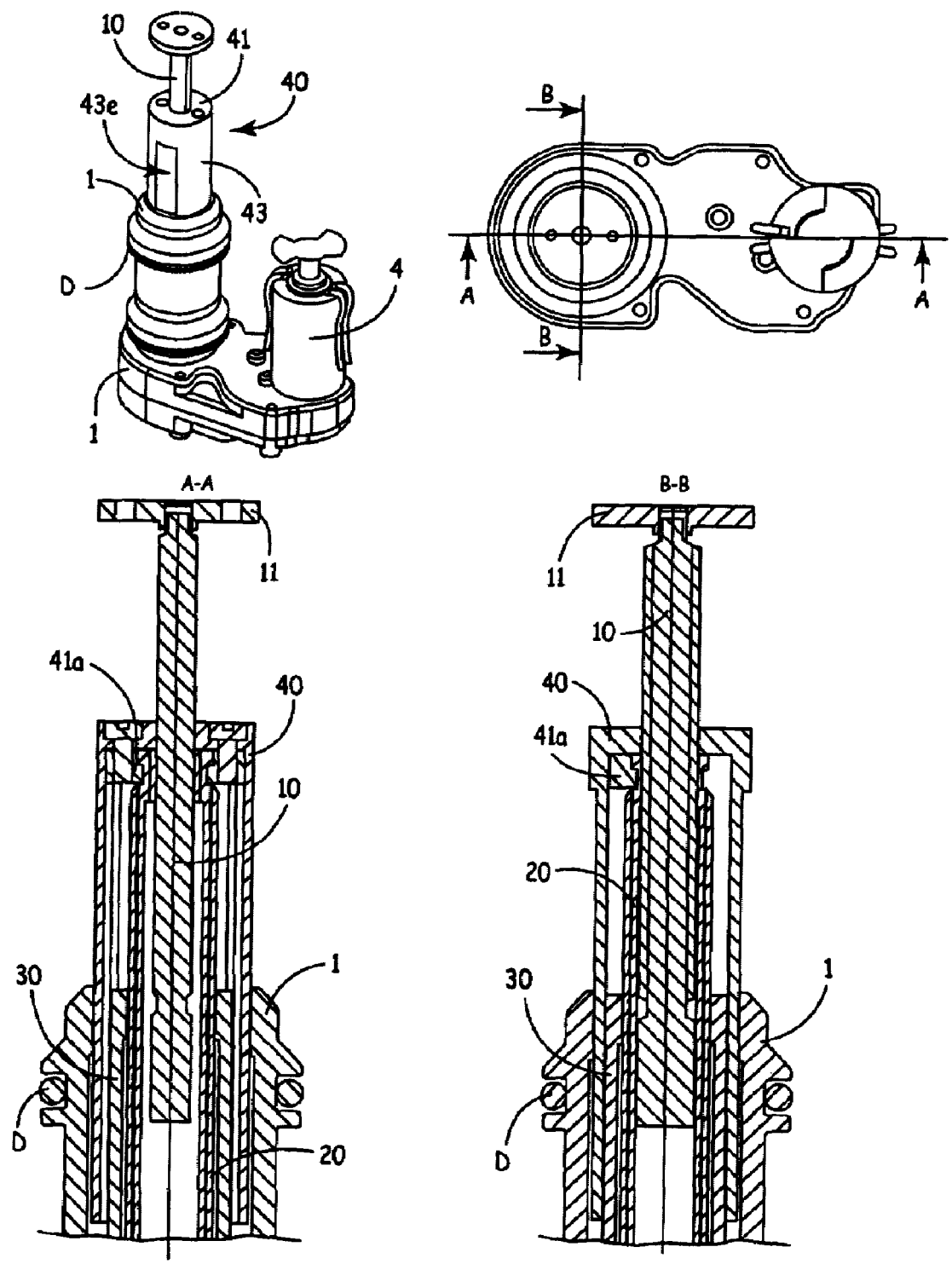
FIG. 25 is an illustration of a seventh example embodiment of a propelling device in accordance with the invention.
Figure 26:
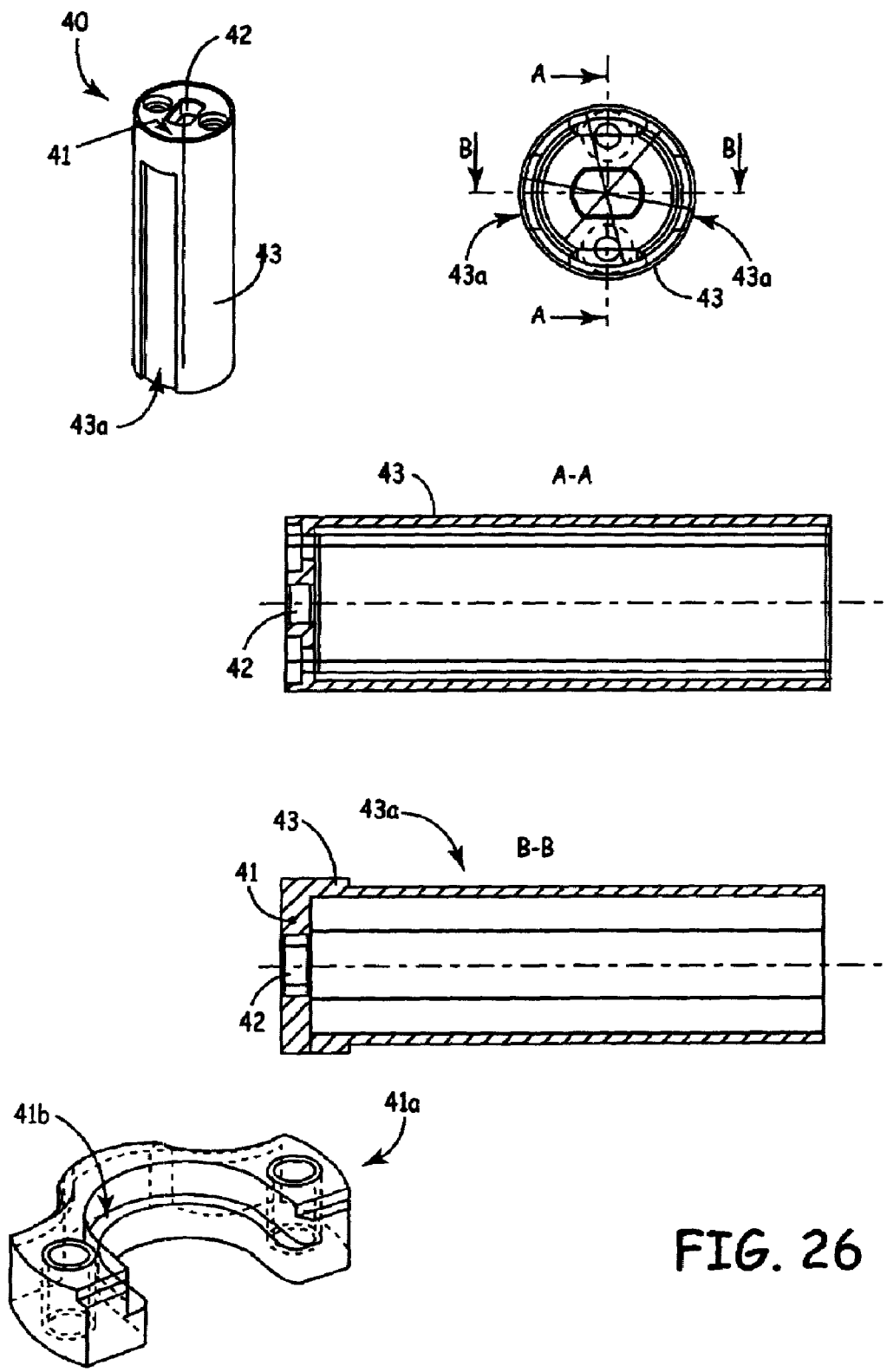
FIG. 26 is an illustration of the anti-rotation lock of the propelling device as shown in FIG. 25.

In extending from the most distal position of the propelling device as shown in FIG. 24, the threaded rod 10 urges the piston K into the syringe body A in the direction V towards the syringe body orifice which in the example embodiment is, still at this time, sealed off tight by a diaphragm. The propelling device is powered by the motor 4 via a spur gear unit 5*a* to 5*f* as well as 33. For further details as to the propelling device, reference is made particularly to the example embodiment as shown in FIGS. 1 to 10. However, instead of this, the other propelling devices as described above may be likewise employed. Thus, for example, the propelling device as shown in FIGS. 19 to 22 could be ideally installed in the space available alongside the syringe body A and the stages of the propelling device. FIGS. 25 and 26 illustrate a seventh example embodiment of the invention having a propelling device which is substantially the same as that of the first example embodiment. FIG. 25 is an illustration of the propelling device in an overall view in perspective, in a view from above with the two entered sections A—A and B—B and parts of these two sections. FIG. 26 is an illustration of an anti-rotation lock 40 in an overall view in perspective as viewed from the rear and in the two sections A—A and B—B as entered. Also evident from FIG. 26 is a slaving element 41*a*, applied to the anti-rotation lock 40, which is a further development of the anti-rotation lock of the first example embodiment.

However, the anti-rotation lock 40 of the seventh example embodiment is not formed by an anti-rotation fork with penetratable linear guiding slots, instead the anti-rotation lock 40 surrounds the part of the propelling device extensible from the base element 1 with the exception of the extended part of the first shifting stage 10. The anti-rotation lock 40 of the seventh example embodiment is configured as a closed sleeve body providing soilage protection, it preferably being made as a ceramic component. Instead of penetration slots, this sleeve body 43 comprises two groove-shaped recesses 43*a* oriented in the longitudinal direction of the sleeve body 43, the linear guiding means of the base element 1 engaging each of these recesses for linear guidance of the anti-rotation lock 40. This linear guidance as such is comparable to that of the first example embodiment. In this example embodiment, two linear recesses 43*a* are provided ending in the proximal circumferential edge of the sleeve body 43. In principle, even a single recess would suffice, however, also more than two recesses 43*a* may be provided.

Inserted in the sleeve body 43 is a slaving element 41*a*, screwed to the disk 41 forming the bottom of the sleeve. As best evident from FIG. 26, the slaving element 41*a* is a partly annular component, semi-circular in the example embodiment, the outer circumferential surface areas are partly in close contact with the inner circumferential surface area of the sleeve body 43 for the purpose of positioning the screw holes. The slaving element 41*a* forms a cuff for the second shifting stage 20 and serves to slave the anti-rotation lock 40 in the movement of the second shifting stage 20. For this purpose, the slaving element 41*a* engages a circumferential recess in the outer shell surface area of the second shifting stage 2(*i* by a flange 41*b* protruding radially inwards from an inner circumferential surface area. The anti-rotation lock 40 is locked from shifting in both the extending direction and the retraction direction at the second shifting stage 20 without, however, obstructing the rotational movement of the second shifting stage 20.

What is claimed is:

1. An apparatus for administering a liquid medicament, comprising a housing, a piston, a container and a propelling device, said propelling device comprising:
    (a) a base element;
    (b) an axially fixed drive member, the drive member being rotatively mounted in the base element;
    (c) a first shifting stage, the first shifting stage being shiftable relative to said base element, wherein said first shifting stage, on shifting, advancing said piston in said container resulting in said liquid medicament being dispensed from said container in a metered manner; and
    (d) a second shifting stage, the second shifting stage being shiftable relative to the drive member wherein the second shifting stage slaves the first shifting stage, thereby forming a first spindle drive;
    wherein the first and said second shifting stages, when seen in said advance direction of said piston, overlap at least in part, the first and second shifting stages together forming a first spindle drive, a rotational movement of which causes the first shifting stage to shift and wherein, the container being mounted in the housing such that the container is prevented from shifting, the piston being held in said container and said first shifting stage being connected to said piston only by exerting contact pressure on said piston.

2. The apparatus of claim 1, wherein the first and said second shifting stages are operably connected by a male thread and a female thread.

3. The apparatus of claim 2, wherein said second shifting stage shifts as a driven member of a second spindle drive.

4. The apparatus of claim 3, wherein said second shifting stage is movably slaved by the a drive member of said second spindle drive.

5. The apparatus of claim 4, wherein a the thread of said second shifting stage with which said second shifting stage engages said drive member of said second spindle drive and a thread of said first shifting stage have the same hand.

6. The apparatus of claim 3, wherein said second shifting stage is rotary driven and forms, together with a reaction member which is non-rotatable relative to said base element, said second spindle drive.

7. The apparatus of claim 3, wherein said first shifting stage is rotary driven and forms, together with said second shifting stage which is non-rotatable relative to said base element, said first spindle drive.

8. The apparatus of claim 1, wherein an axis of rotation of said two spindle drives are in alignment.

9. The apparatus of claim 2, wherein said first shifting stage and a shifting axis of said second shifting stage are parallel to each other.

10. The apparatus of claim 3, wherein said first shifting stage is rotationally driven by the drive member via a spur gear unit.

11. The apparatus of claim 10, wherein one of said first shifting stage and said second shifting stage is prevented from rotating relative to said base element by an anti-rotation lock.

12. The apparatus of claim 11, wherein said anti-rotation lock is formed by a slipper having at least one sliding surface area relative to said base element and at least one sliding surface area relative to said first shifting stage, said sliding surface areas permitting shifting and preventing a rotation of said first shifting stage relative to said base element.

13. The apparatus of claim 12, wherein said slipper is jointly shifted together with said second shifting stage.

14. The apparatus of claim 13, wherein said anti-rotation lock comprises a sleeve body substantially surrounding said propelling device.

15. An apparatus for administering a substance, comprising a housing, a piston, a container and a propelling device, the propelling device comprising:
- a base element;
- a first shifting stage shiftable relative to said base element; and
- a second shifting stage shiftable relative to said base element and to said first shifting stage, the first and second shifting stages together forming a first spindle drive, rotational movement of which causes the first shifting stage to shift, a portion of the first shifting stage being in contact with the piston;
- wherein said propelling device and the container and piston are operably coupled to the housing, the container being mounted in the housing such that the container is prevented from shifting, wherein the propelling device and the container being separately accommodated in the housing whereby either the container, the propelling device or both can be exchanged.

16. The apparatus according to claim 15, wherein said first and said second shifting stages are operably coupled by respective complementary threaded portions to form a first spindle drive, a rotational movement of which causes said first shifting stage to shift.

17. The apparatus according to claim 16, further comprising a second spindle drive, wherein said second shifting stage shifts as a driven member of the second spindle drive.

18. The apparatus according to claim 17, wherein said second shifting stage is substantially slaved in both rotation and shift by said second spindle drive.

19. The apparatus according to claim 18, wherein said first and second shifting stages overlap in part.

20. An apparatus for administering a liquid medicament, said apparatus comprising:
- a housing;
- a reservoir for the liquid medicament;
- a piston which, by advancing, dispenses the liquid medicament from the reservoir in a metered manner; and
- a propelling device, comprising:
  - a shifting stage shiftable relative to the housing and advancing, on shifting, the piston in the container, resulting in liquid medicament being dispensed from the container in a metered manner, and comprising a thread;
  - a drive member, rotationally mounted by the housing and comprising a thread; and
  - a threaded sleeve shiftable relative to the housing as well as relative to the shifting stage in the advance direction of the piston and slaving the shifting stage in its shifting movement in the advance direction of the piston, and comprising an inner thread and an outer thread, one of which is in a first threaded engagement with the thread of the shifting stage and the other of which is in a second threaded engagement with the thread of the drive member, wherein the drive member is a drive sleeve surrounding the threaded sleeve and its thread is an inner thread in the second threaded engagement with the outer thread, and wherein the threaded sleeve surrounds the shifting stage and its inner thread is in the first threaded engagement with the thread of the shifting stage.

21. The apparatus of claim 20, wherein said first and second shifting stages are operably connected by a male thread and a female thread, said second shifting stage shifting as a driven member of a second spindle drive, said second spindle drive comprising the driven member and a drive member, said second shifting stage is movably slaved by the drive member of said second spindle drive.

22. The apparatus of claim 21, wherein a thread of said second shifting stage with which said second shifting stage engages said drive member of said second spindle drive and a thread of said first shifting stage have the same hand.

23. The apparatus of claim 21, wherein said second shifting stage is rotary driven and forms, together with a reaction member which is non-rotatable relative to said housing, said second spindle drive.

24. The apparatus of claim 21, wherein said first shifting stage is rotationally driven by the drive member via a spur gear unit and one of said first shifting stage and said second shifting stage is prevented from rotating relative to said housing by an anti-rotation lock formed by a slipper having at least one sliding surface area relative to said housing and at least one sliding surface area relative to said first shifting stage, said sliding surface areas permitting shifting and preventing a rotation of said first shifting stage relative to said housing.

25. The apparatus of claim 24, wherein said slipper is jointly shifted together with said second shifting stage.

26. The apparatus of claim 25, wherein said anti-rotation lock comprise a sleeve body substantially surrounding said propelling device.

* * * * *